(12) United States Patent
Le Moal

(10) Patent No.: US 9,588,059 B2
(45) Date of Patent: Mar. 7, 2017

(54) METHOD FOR ANALYZING THE QUALITY OF A GLAZING

(75) Inventor: Simon Le Moal, Paris (FR)

(73) Assignee: SAINT-GOBAIN GLASS FRANCE, Courbevoie (FR)

( * ) Notice: Subject to any disclaimer, the term of this patent is extended or adjusted under 35 U.S.C. 154(b) by 392 days.

(21) Appl. No.: 14/113,323

(22) PCT Filed: Apr. 6, 2012

(86) PCT No.: PCT/FR2012/050757
§ 371 (c)(1),
(2), (4) Date: Oct. 22, 2013

(87) PCT Pub. No.: WO2012/143649
PCT Pub. Date: Oct. 26, 2012

(65) Prior Publication Data
US 2014/0050388 A1 Feb. 20, 2014

(30) Foreign Application Priority Data
Apr. 22, 2011 (FR) ..................... 11 53514

(51) Int. Cl.
*G06K 9/00* (2006.01)
*G01N 21/95* (2006.01)
(Continued)

(52) U.S. Cl.
CPC ......... *G01N 21/95* (2013.01); *G01B 11/2513* (2013.01); *G01M 5/0033* (2013.01);
(Continued)

(58) Field of Classification Search
None
See application file for complete search history.

(56) References Cited

U.S. PATENT DOCUMENTS 6,100,990 A    8/2000   Ladewski
2003/0091224 A1*   5/2003   Wiley .................... G06T 7/001
                                                                   382/145
(Continued)

FOREIGN PATENT DOCUMENTS

EP    0 924 494      6/1999
JP    63-100308 A   5/1988
(Continued)

OTHER PUBLICATIONS

International Search Report Issued May 31, 2012 in PCT/FR12/50757 Filed Apr. 6, 2012.
(Continued)

*Primary Examiner* — Sumati Lefkowitz
*Assistant Examiner* — David Perlman
(74) *Attorney, Agent, or Firm* — Oblon, McClelland, Maier & Neustadt, L.L.P.

(57) ABSTRACT

A method for analyzing quality of a glazing including: generating at least one digital image of a test chart produced in reflection by an external surface of the glazing on an outside of the glazing; computation by at least one processing unit of quantities representative of the quality of the glazing based on the at least one image generated; and comparing values computed for the representative quantities with respect to reference values. The test chart exhibits a pattern including elements of closed contours arranged periodically. The representative quantities are representative of a deformation of the image of the test chart produced in reflection by the external surface of the glazing on the outside of the glazing, and the computation of a representative quantity includes the computation of a density of the elements.

14 Claims, 3 Drawing Sheets

(51) Int. Cl.
  *G01B 11/25* (2006.01)
  *G01M 5/00* (2006.01)
  *G01N 21/958* (2006.01)
  *G06K 9/48* (2006.01)

(52) U.S. Cl.
  CPC ........ *G01M 5/0091* (2013.01); *G01N 21/958* (2013.01); *G06K 9/48* (2013.01); *G01N 2021/9586* (2013.01)

(56) References Cited

U.S. PATENT DOCUMENTS

2006/0050284 A1 3/2006 Bertin-Mourot et al.
2009/0279772 A1* 11/2009 Sun ...................... G06K 9/6298
  382/141
2010/0309328 A1 12/2010 Ehrick
2013/0004719 A1 1/2013 Thellier et al.

FOREIGN PATENT DOCUMENTS

| JP | 4666273 B1 | 4/2011 |
| WO | 02 42715 | 5/2002 |
| WO | 2009 102490 | 8/2009 |
| WO | 2011 145168 | 11/2011 |

OTHER PUBLICATIONS

Japanese Office Action issued Dec. 15, 2015, in corresponding Japanese Patent Application No. 2014-505695. English translation provided.

\* cited by examiner

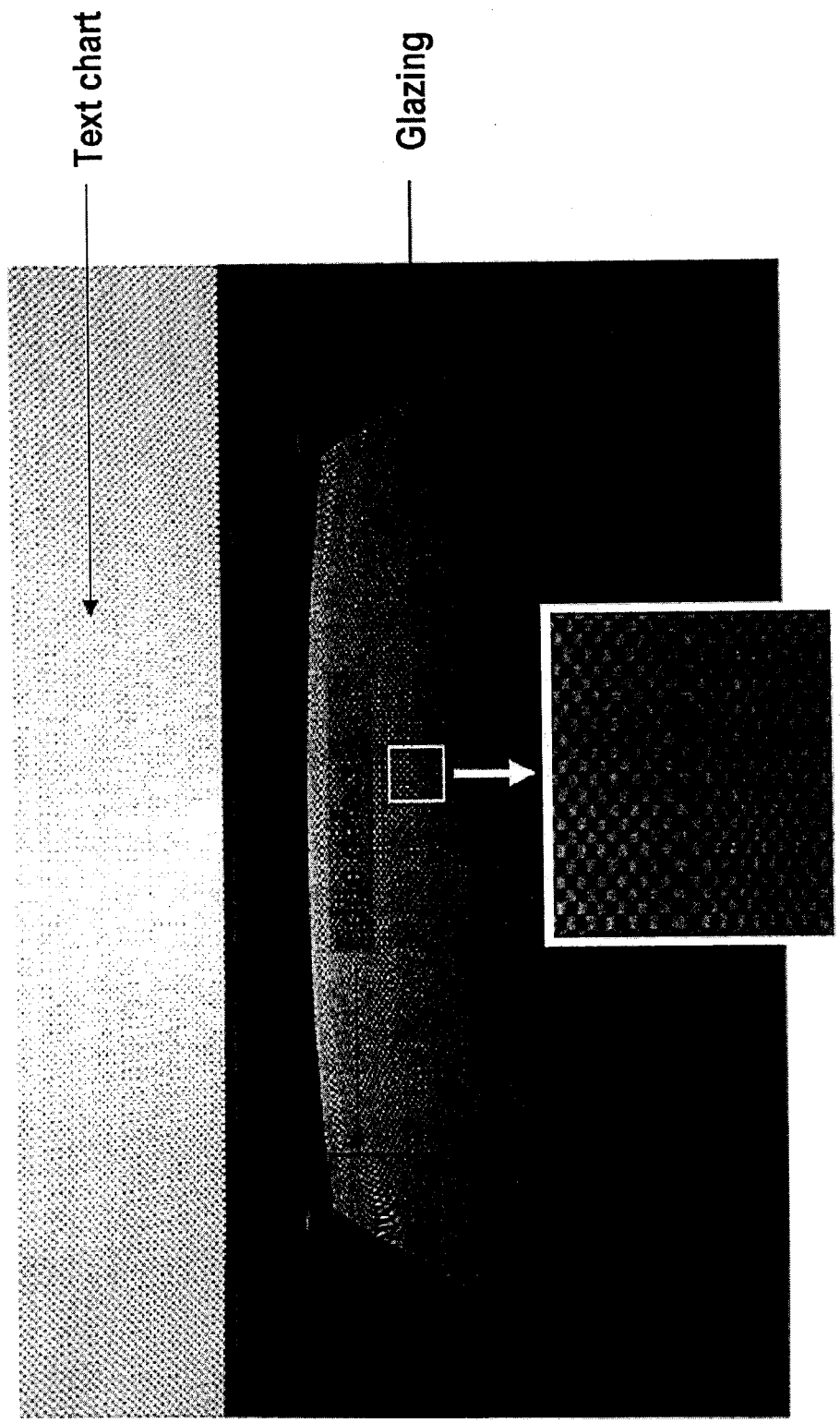

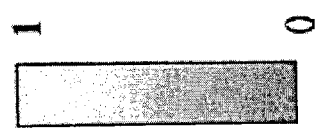
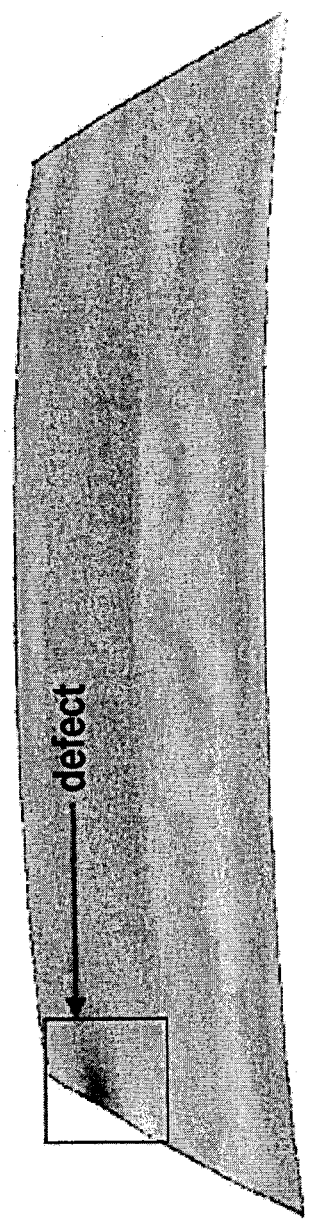
Figure 4
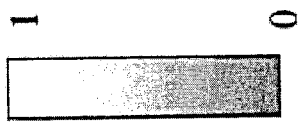
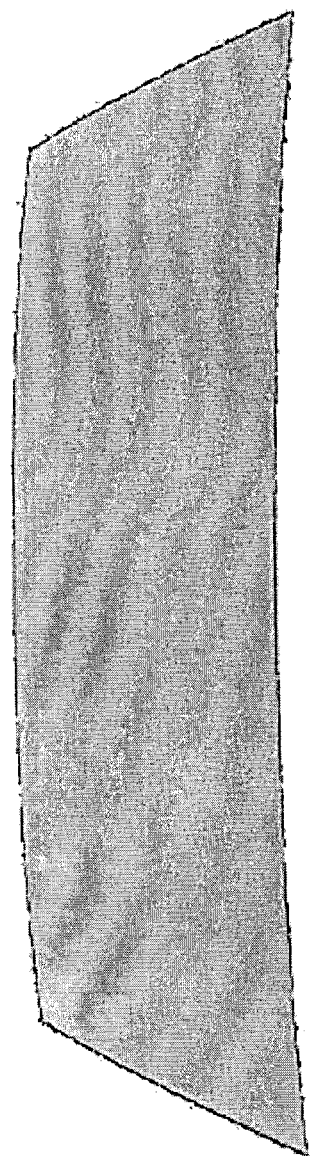
Figure 5

METHOD FOR ANALYZING THE QUALITY OF A GLAZING

BACKGROUND

The present invention relates to the field of the analysis of the quality of glazings, especially automobile glazings.

The present invention relates more particularly to a method for analyzing the quality of a glazing, comprising:
- a step of generating a digital image of a test chart produced in reflection by the external surface of the glazing on the outside, the test chart exhibiting a pattern composed of a plurality of contrasted elements defining interface lines therebetween;
- a step of computing quantities representative of the glazing on the basis of the image generated, the computation being performed by a processing unit; and
- a step of comparing the values computed for the representative quantities with respect to reference values.

WO-A-02/42715 describes a method for analyzing the surface of a glazing consisting in extracting, by digital processing and for each pixel of the digitized image, local phases in two directions. The variations of the local phases make it possible to compute variations of local slopes of the surface of the glazing so as to deduce therefrom variations of curvature or variations of altitude of the surface.

It is possible, by comparing the curvature variations of the glazing with reference values, to proceed to the choice of the rejection of the glazing.

Nonetheless, whereas this possible selection criterion does admittedly allow appraisal of the curvature and the altitude of the glazing, it does not necessarily allow appraisal of the esthetic quality of the image produced in reflection by the glazing. Indeed, the esthetics do not depend only on the geometry of the glazing, but also, for example, on the position of observation.

If it were attempted to use such a method to appraise the esthetic quality of the glazing in reflection, certain glazings would sometimes be rejected without, however, exhibiting actual esthetic impairment or vice versa.

Furthermore, with a method of this type, the values computed on the edges of the glazing are generally not reliable.

Finally, this type of method requires lengthy and irksome calibration.

WO-A-2007/115621 and U.S. Pat. No. 6,392,754 also describe methods aimed at measuring the shape of the surface of the glazing. These methods exhibit in particular the same drawback as regards relevance of the assessment of the esthetic quality of the glazing.

BRIEF SUMMARY

An aim of the invention is to provide a method for analyzing the quality of the image produced in reflection by the external surface of a glazing which makes it possible to choose to reject the glazing on the basis of technical criteria which are relevant in respect of the assessment of the esthetic quality in reflection of the glazing viewed from the outside.

According to one aspect of the invention, it entails a method for analyzing the quality of a glazing, comprising:
- a step of generating at least one digital image of a test chart produced in reflection by the external surface of the glazing on the outside of the glazing;
- a step of computation by at least one processing unit of quantities representative of the quality of the glazing on the basis of the at least one image generated; and
- a step of comparing the values computed for the representative quantities with respect to reference values, in which the test chart exhibits a pattern comprising elements of closed contours arranged periodically, in which the representative quantities are representative of a deformation of the image of the test chart produced in reflection by the external surface of the glazing on the outside of the glazing and in which the step of computing a representative quantity includes the computation of a density of the elements.

The advantage of this method is that it makes it possible to assess the quality of the image in reflection produced by a glazing, not on the basis of dimensional characteristics of the glazing, but based on the image in reflection produced by the external surface of the glazing from the outside. The choice of the rejection of the glazing is then relevant from the viewpoint of the assessment of the esthetic quality of the image produced in reflection on the outside by the glazing.

By virtue of this method, the rejection of a glazing which exhibits a geometric defect that is not visible and/or which is not assessed as unesthetic is avoided. Conversely, it enables better selection of a glazing that does not exhibit any significant surface defect but nevertheless produces an appreciable esthetic defect in the image produced in reflection.

The method furthermore makes it possible to evaluate the defects on any zone of the glazing, especially on the edges of the glazing.

The method also allows an analysis without calibration.

Another advantage of the method is its robustness to various types of defects, elongate or otherwise, and its robustness to the direction of the defects.

According to particular embodiments, the method comprises one or more of the following characteristics, taken in isolation or in accordance with all the technically possible combinations:
- the elements are arranged periodically in at least two directions;
- the elements have a larger dimension of less than or equal to 50 mm, preferably less than or equal to 20 mm, preferably less than or equal to 10 mm;
- the elements are of identical contours;
- the processing unit analyses a zone Z of the image comprising at least five elements;
- in which for each pixel $P_k$ of a predefined zone Z of the image, the processing unit computes a value representative of a local density of the elements in the neighborhood $V_k$ of each pixel $P_k$;
- the neighborhood $V_k$ is a zone including several pixels around the pixel $P_k$ and with the pixel $P_k$ as center;
- the computation is repeated inside one or more predefined zones Z of analysis of the image;
- at least one of said representative quantities is a local statistical quantity computed on the basis of values representative of local density of the elements in the neighborhood $V'_k$ of each pixel $P_k$;
- at least one of said representative quantities is a global statistical quantity computed on the basis of values of local statistical quantities over at least one of the analysis zones Z;
- the computation of the local or global statistical quantity includes the computation of one of the following quantities, taken in isolation or in any possible combination: an average, a weighted average, a median, a number of occurrences above or below a reference value, a maximum, a minimum, a standard deviation or the deviation between a maximum and a minimum;

the elements are non-adjoining and contrasted;

the elements are round or checkers in the shape of a polygon, for example in the shape of a triangle or parallelogram, for example in the shape of a lozenge or square;

in which the elements are adjoining and contrasted checkers forming a checkerboard;

the elements are defined by strands of a grid;

the elements are in the shape of a polygon, for example in the shape of a parallelogram, for example in the shape of a lozenge or square;

the method is repeated with at least one additional image of the same glazing, different from the first image;

the additional image is obtained for a test chart identical to the first image but whose pattern is rotated in the plane of the test chart by an angle of at least 20°;

the angle of incidence ($\alpha$) between the apparatus and the normal to the plane of the glazing is between 0° and 90°, preferably between 40° and 70° for a motor vehicle lateral glazing, and preferably between 60° and 80° for a motor vehicle roof;

the angle of incidence ($\alpha$) between the axis of the apparatus and the normal to the plane of the glazing is equal to the angle ($\beta$) between the plane of the test chart and the plane of the glazing;

the glazing is inwardly curved;

the step of generating the image comprises:

a step of exposing the glazing to a test chart exhibiting a pattern composed of a plurality of contrasted elements;

a step of digital acquisition by an apparatus with digital sensors, of the image reflected by the glazing toward the apparatus;

the image of a test chart produced in reflection by the glazing is obtained by a simulation on the basis of the external surface of the glazing, for example on the basis of a theoretical surface of the glazing, on the basis of a measured surface of the glazing or else on the basis of a surface obtained by simulation of the bending of the glazing;

the method comprises a step of choosing rejection of the glazing as a function of the result of the comparison.

According to another aspect of the invention, it entails a method for manufacturing a glazing comprising a method for forming the glazing followed by a method for analyzing the quality of the glazing formed, in which the method for analyzing the quality of the glazing is such as described hereinabove.

According to a particular embodiment, the method for manufacturing the glazing comprises a step of bending the glazing.

Another aspect of the invention relates to a device for analyzing the quality of a glazing, comprising means for generating a digital image of a test chart produced in reflection by the external surface of the glazing on the outside of the glazing and a processing unit for processing the image generated, the processing unit comprising a memory and a computer, in which the memory comprises programs able to implement the method such as described hereinabove, the programs being able to compute quantities representative of the glazing on the basis of the image generated, the representative quantities being representative of a deformation of the image of the test chart produced in reflection by the external surface of the glazing on the outside of the glazing and comprising a quantity representative of a local density of the elements.

According to a particular embodiment of the device, the means for generating the image comprise a test chart and an apparatus with digital sensors, the test chart and the apparatus being designed to respectively produce and acquire the image of the test chart produced in reflection by the external surface of the glazing, the test chart being for example a screen, the device comprising for example a projector for projecting a test chart pattern onto the screen.

BRIEF DESCRIPTION OF THE DRAWINGS

The invention will be better understood on reading the description which follows, given solely by way of example, while referring to the appended drawings in which:

FIG. 3 is a perspective view illustrating a glazing exposed to a digital image obtained in reflection for a glazing illuminated by a test chart according to FIG. 2, the test chart being visible in the background;

FIG. 4 illustrates the image of FIG. 3 after processing by an algorithm; and

FIG. 5 illustrates an image analogous to FIG. 4 for a glazing not possessing any esthetic defect in reflection.

DETAILED DESCRIPTION

Figure 1:
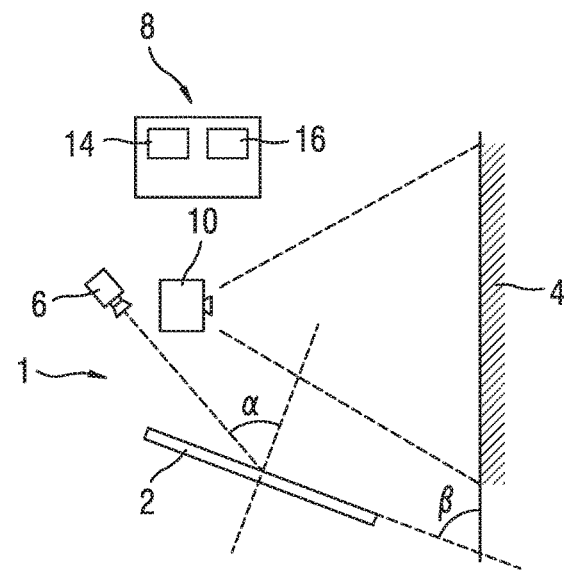
FIG. 1 is a schematic view illustrating a device for analyzing quality of a glazing, according to invention.

FIG. 1 illustrates a device 1 suitable for undertaking an analysis of the quality of the image produced in reflection by the external surface of a glazing 2, on the outside of the glazing.

The device comprises a test chart 4, a digital snapshot apparatus 6, and a processing unit 8 for the image produced by the apparatus 6.

Figure 2:
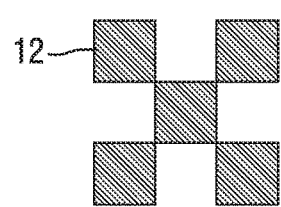
FIGS. 2, 2A and 2B are schematic views illustrating examples of test chart pattern.

The test chart pattern illustrated in FIG. 2 is a checkerboard composed of contrasted, for example alternately dark and light, square checkers.

As a variant, the checkers have a shape of any suitable type, for example a shape of a polygon, for example a triangle or parallelogram, for example a square or lozenge. In a general way, it entails a pattern of adjoining and contrasted checkers forming a checkerboard.

Figure 2A:
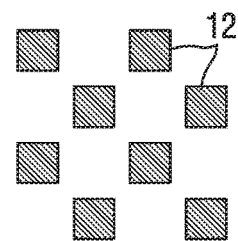
Figure 2B:
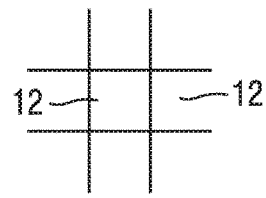

FIGS. 2A and 2B illustrate possible variants of patterns.

It should be noted that the examples of patterns provided are nonlimiting. Furthermore, the black and white colors may be reversed, that is to say the negatives of the test chart patterns illustrated may be used.

FIG. 2A illustrates a pattern composed of contrasted square checkers, spaced apart (or non-adjoining) and aligned along their diagonals.

As a variant, the checkers have a shape of any suitable type for example a shape of a polygon, for example a triangle or parallelogram, for example a square or lozenge. Round contrasted elements constitute a variant.

In a general way, the elements are closed contour elements. The elements are spaced apart and arranged periodically in at least one direction, for example in two for example perpendicular directions.

The pattern of FIG. 2B is a pattern of square checkers defined by a crisscross.

As a variant, the checkers have a shape of any suitable type for example a shape of a polygon, for example triangle or parallelogram, for example square or lozenge.

In a general way the elements are elements of closed contours defined by the strands of a grid, the elements being arranged periodically in at least one direction, for example in two for example perpendicular directions.

In the three cases of FIGS. 2 to 2B, in a general way, the pattern is one comprising elements of closed and identical contours arranged periodically, preferably arranged periodically in at least two for example perpendicular directions.

In a preferred manner, the elements are of identical shapes and/or of the same dimensions.

In a preferred manner also, the elements have a larger dimension of less than or equal to 50 mm, preferably less than or equal to 20 mm, preferably less than or equal to 10 mm.

A test chart with a pattern according to FIG. 2 and 6 mm×6 mm sided elements has produced the images of FIGS. 3 and 4.

In a general way, the dimensions of the elements are, however, of any suitable type.

The test chart is for example composed of a single pattern such as illustrated in FIGS. 2 to 2B. As a variant, the test chart exhibits several patterns in predetermined zones.

The test chart preferably has dimensions and a positioning that are suitable for generating an image over the whole of the surface of the glazing.

The test chart 4 is here a screen onto which an image is projected by a projector 10.

The test chart 4 is preferably plane. The digital apparatus 6, which is for example a camera (or photographic apparatus) with CCD sensors, is arranged so as to receive the image in reflection of the test chart 4. In the example illustrated, the apparatus 6 is placed on the opposite side from the test chart 4 with respect to the glazing 2.

The angle $\alpha$ between the axis of the digital apparatus 6 and the normal to the plane of the glazing 2 is between 020 and 90° with the surface of the glazing 2. This angle is for example between 40° and 70° for a motor vehicle lateral glazing, for example about 60°, so as to be as close as possible to the actual conditions of observation. For a motor vehicle roof, this angle will be for example between 60° and 80°, for example about 75°. An angle of more than for example 40° makes it possible to reduce the disturbances, if any, due to secondary reflections. Concerning the test chart 4, note that the angle $\beta$ between the plane of the test chart 4 and the plane of the glazing 2 is preferably equal to the angle $\alpha$ between the axis of the digital apparatus 6 and the normal to the plane of the glazing 2.

In the case of an inwardly curved glazing, the plane tangent to the center of the glazing 2 will be considered for example to be the plane of the glazing 4.

The digital apparatus 6 provides the processing unit 8 with a digitized image of the image in reflection of the test chart 4 produced by the glazing 2.

The raw image produced by a glazing 2 is illustrated in FIG. 3. This example more particularly entails a motor vehicle roof.

The digitally acquired image is thereafter processed in an automated manner by the processing unit 8, for at least one predefined zone Z of the image. It should be noted that, in the example illustrated in FIGS. 3 and 4, the zone Z corresponds to the whole of the image produced by the glazing, but that it may entail several distinct zones Z, in particular disjoint zones.

The processing unit 8 comprises a memory 14 on which are recorded processing programs, and a computer 16 suitable for executing the processing programs.

The processing programs are able to carry out, by means of the computer 16, computations of quantities representative of a deformation of the image produced in reflection by the glazing 2.

The representative quantities are thereafter used to choose to reject the glazing 2 as a function of the result of the comparison between the values computed for the corresponding glazing 2 and reference values.

The reference values are for example obtained by measurement and computation on reference samples.

The quantities are more particularly, in the example described, representative of a local density of the elements making up the test chart. This constitutes an essential characteristic of the invention.

The local density of the elements making up the test chart at a pixel $P_k$ of the image is for example obtained by computing the density of the elements in a neighborhood $V_k$ of the pixel $P_k$. The neighborhood $V_k$ is a zone which includes pixels surrounding the pixel and is for example centered on the pixel $P_k$.

In a preferred manner, for each pixel $P_k$ of a predefined zone Z of the image, the processing unit computes a value representative of a local density of the elements in the neighborhood $V_k$ of each pixel $P_k$.

The neighborhoods $V_k$ are for example all of identical dimensions.

The local density value is for example obtained by an average of the number of pixels belonging to the contour of the elements in the neighborhood. The pixels of contours/edges are for example detected by means of a Canny filter applied to the image as gray levels.

A variant in respect of the density computation consists in carrying out a statistical computation on the neighborhood, for example a standard deviation of the gray levels of the image. According to another variant, a frequency analysis of the elements is undertaken, for example by means of a Fourier transform on the gray levels.

Each pixel $P_k$ is thus for example assigned a value of local density of the elements in a neighborhood of the pixel $P_k$.

FIG. 4 illustrates the image of FIG. 3 after processing. Zones which are more or less colored (gray levels in FIGS. 4 and 5) are visible, corresponding to ordered values of local densities of the elements.

Indeed, to visually emphasize the values of local density of the elements, each pixel of the image has been colored as a function of its value. The pixels corresponding to high values of local density appear lighter.

In a second computation step, the program is such that the processing unit 8 computes a local standard deviation E or a local Rate of Change RoC (or rate of variation) of local density of the elements for each pixel of the image inside each analysis zone Z.

To carry out this computation, in the same manner as previously, a neighborhood $V'_k$ is defined for each pixel $P_k$.

The value obtained is assigned to each pixel $P_K$.

The neighborhood $V'_k$ is a zone which includes pixels surrounding the pixel and is for example centered on the pixel $P_k$. It is for example the same neighborhood as the neighborhood $V_k$.

In a preferred manner, for each pixel $P_k$ of a predefined zone Z of the image, the processing unit computes a value representative of a variation of local density of the elements in the neighborhood $V'_k$ of each pixel $P_k$.

The neighborhoods $V'_k$ are for example all of identical dimensions.

Note that the local rate of change RoC is for example obtained by computing the difference between the maximum value of local density in the neighborhood $V'_k$ and the minimum value.

As a variant, the statistical quantity is for example a weighted average, a median, a maximum, a minimum, a number of occurrences above or below a reference value, another statistical quantity of any suitable type, or else a combination of several of these quantities, of any suitable type.

In a third step, a global statistical quantity is for example computed on the basis of the local statistical quantities.

This entails for example computing the maximum, over the analysis zone Z, of the local statistical quantity of all the pixels $P_k$ of the analysis zone Z.

As a variant, the statistical quantity is a weighted average, a median, a minimum, a deviation between a maximum and a minimum, a number of occurrences above or below a reference value, another statistical quantity of any suitable type, or else a combination of several of these quantities, of any suitable type.

In a general way it is thus a statistical quantity of local density of the elements, that is to say a statistical quantity computed on the basis of several values of local densities of the elements.

It should however be noted that, even if statistical quantities are preferred, as a variant raw values may be involved, which are compared directly with reference values.

In FIGS. 3 and 4, the maximum of local rate of change RoC of local density of the elements has been computed. It is markedly greater for FIG. 3 than for FIG. 4 (with a ratio of 7 between the two figures), thereby confirming the relevance of this criterion, the glazing 2 of FIG. 3 presenting a defect at the level of an edge.

For each glazing 2, and each analysis zone Z, the value of global statistical quantity is compared with a reference value. The processing programs of the unit 8 are for example able to perform this comparison. The reference values are defined for each zone Z and are for example different for different zones Z.

The result of the comparison will lead for example to the rejection of the glazing 2 of FIG. 3.

As a variant, a different number of analysis zones Z is defined. The number, the position and the extent of the analysis zone or zones Z are chosen from any suitable type.

In addition to the device described hereinabove, the subject of the invention is also the method implementing the device hereinabove, namely, in a general way, a method comprising:
  a step of generating a digital image of the test chart 4 produced in reflection by the external surface of the glazing 2 on the outside of the glazing 2;
  a step of computation by the processing unit 8 of quantities representative of the quality of the glazing 2 on the basis of the image generated; and
  a step of comparing the values computed for the representative quantities with respect to reference values.

The test chart 4 exhibits a pattern comprising elements of closed and identical contours arranged periodically, in which the representative quantities are representative of a deformation of the image of the test chart produced in reflection by the external surface of the glazing on the outside of the glazing and in which the step of computing a representative quantity includes the computation of a density of the elements, for example a local density of the elements.

According to particular embodiments, the method according to the invention exhibits the characteristics described hereinabove.

As a variant, the method is implemented for at least one additional image, for example one additional image, so as to make the choice of rejection as a function of the results obtained for the various images.

The additional image is for example obtained by means of an additional camera, with synchronized acquisition, for example simultaneous.

As a variant, the additional image is obtained with the same camera but after displacement of the camera, of the glazing or of the test chart.

As a variant again, the additional image is obtained without displacing the camera and the glazing but after modification of the pattern of the test chart or modification of the angle of the plane of the test chart with respect to the glazing.

The reference values are for example obtained by a simulation on the basis of the external surface of the glazing, for example on the basis of a theoretical surface of the glazing, on the basis of a measured surface or else on the basis of a surface obtained by simulation of the bending of the glazing. The use of a test chart and of a digital apparatus is then not necessary.

As a variant, the reference values are computed on the basis of an image acquired on a reference glazing.

As a variant again, the image of contrasted elements is not obtained by projection onto a screen but by a test chart which is in itself contrasted.

As a variant also, the method according to the invention is combined with a method of known type computing the altitude of the external surface of the glazing. The two methods can indeed provide complementary information.

The invention claimed is:

1. A method for analyzing the quality of a glazing, comprising:
  generating at least one digital image of a test chart produced in reflection by an external surface of the glazing on an outside of the glazing;
  computing, by at least one processing unit, quantities representative of the quality of the glazing based on the at least one image generated, including dividing the image into a plurality of zones and, for at least one of the zones, computing a local density for each pixel based on a neighborhood of the pixel, the neighborhood including the pixel and plural pixels surrounding the pixel with the pixel as a center of the neighborhood, and after the computing a local density for each pixel, computing a local statistical quantity for each pixel in the zone by determining a local standard deviation or a local rate of change of the local density for each pixel in the zone;
  comparing values computed for the representative quantities with respect to reference values;
  in which the test chart exhibits a pattern comprising elements of closed contours arranged periodically, and in which the representative quantities are representative of a deformation of the image of the test chart produced in reflection by the external surface of the glazing on the outside of the glazing.

2. The method as claimed in claim 1, in which the elements are arranged periodically in at least two directions.

3. The method as claimed in claim 1, in which the elements have a larger dimension of less than or equal to 50 mm.

4. The method as claimed in claim 1, in which the elements are of identical contours.

5. The method as claimed in claim 1, in which the one of the zones of the image comprises at least five elements.

6. The method as claimed in claim 1, in which the computing a local density is repeated inside each of the plurality of zones of the image.

7. The method as claimed in claim 1, in which at least one of the representative quantities is a global statistical quantity computed based on values of the local statistical quantities over at least one of the zones.

8. The method as claimed in claim 7, in which the computation of the local or global statistical quantity includes computation of one of the following quantities, taken in isolation or in any possible combination: an average, a weighted average, a median, a number of occurrences above or below a reference value, a maximum, a minimum, a standard deviation, or the deviation between a maximum and a minimum.

9. The method as claimed in claim 1, in which the elements have a larger dimension of less than or equal to 20 mm.

10. The method as claimed in claim 1, in which the elements have a larger dimension of less than or equal to 10 mm.

11. The method as claimed in claim 1, further comprising, after the computing a local statistical quantity for each pixel in the zone, computing a global statistical quantity for the zone based on one or more of a maximum, a weighted average, a median, a minimum, a deviation between a maximum and a minimum, and a number of occurrences above or below a reference value of the local density for each pixel in the zone.

12. The method as claimed in claim 11, wherein the comparing values includes comparing the global statistical quantity for the zone with a reference quantity.

13. A device for analyzing the quality of a glazing, comprising:
means for generating a digital image of a test chart produced in reflection by an external surface of the glazing on an outside of the glazing; and
a processing unit for processing the image generated, the processing unit comprising a memory and a computer, the processing unit being configured to:
compute, quantities representative of the quality of the glazing based on the at least one image generated, including dividing the image into a plurality of zones and, for at least one of the zones, computing a local density for each pixel based on a neighborhood of the pixel, the neighborhood including the pixel and plural pixels surrounding the pixel with the pixel as a center of the neighborhood, and after the computing a local density for each pixel, computing a local statistical quantity for each pixel in the zone by determining a local standard deviation or a local rate of change of the local density for each pixel in the zone; and
compare values computed for the representative quantities with respect to reference values;
in which the test chart exhibits a pattern comprising elements of closed contours arranged periodically, and
in which the representative quantities being representative of a deformation of the image of the test chart produced in reflection by the external surface of the glazing on the outside of the glazing.

14. A method for analyzing the quality of a glazing, comprising:
generating at least one digital image of a test chart produced in reflection by an external surface of the glazing on an outside of the glazing;
computing, by at least one processing unit, quantities representative of the quality of the glazing based on the at least one image generated, including dividing the image into a plurality of zones and, for at least one of the zones computing a local density for each pixel based on a neighborhood of the pixel, the neighborhood including the pixel and plural pixels surrounding the pixel with the pixel as a center of the neighborhood; and
comparing values computed for the representative quantities with respect to reference values;
in which the test chart exhibits a pattern comprising elements of closed contours arranged periodically, and
in which the representative quantities are representative of a deformation of the image of the test chart produced in reflection by the external surface of the glazing on the outside of the glazing, and
in which the computing the local density for each pixel includes calculating an average based on a number of pixels in the neighborhood of the pixel that belong to a contour of the elements.

* * * * *